United States Patent
Perry et al.

(10) Patent No.: US 7,875,240 B2
(45) Date of Patent: *Jan. 25, 2011

(54) AUTO-CALIBRATION LABEL AND METHOD OF FORMING THE SAME

(75) Inventors: Joseph E. Perry, Osceloa, IN (US); Andrew J. Edelbrock, Granger, IN (US); Russell J. Micinski, South Bend, IN (US); Steven C. Charlton, Osceloa, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/918,830

(22) PCT Filed: Apr. 18, 2006

(86) PCT No.: PCT/US2006/014866

§ 371 (c)(1), (2), (4) Date: Oct. 18, 2007

(87) PCT Pub. No.: WO2006/113865

PCT Pub. Date: Oct. 26, 2006

(65) Prior Publication Data

US 2009/0041625 A1    Feb. 12, 2009

Related U.S. Application Data

(60) Provisional application No. 60/672,764, filed on Apr. 19, 2005.

(51) Int. Cl.
*G01N 21/00* (2006.01)

(52) U.S. Cl. ............ 422/64; 422/62; 422/63; 422/65; 422/99; 422/100; 436/180

(58) Field of Classification Search ........... 422/99–100, 422/62–65; 436/180
See application file for complete search history.

(56) References Cited

U.S. PATENT DOCUMENTS 5,366,609 A    11/1994    White et al. ............... 204/403
(Continued)

FOREIGN PATENT DOCUMENTS

EP    0 840 122 A2    5/1998
(Continued)

OTHER PUBLICATIONS

Written Opinion corresponding to International Patent Application Serial No. PCT/US2006/014866, European Patent Office, dated Oct. 26, 2006, 5 pages.
(Continued)

*Primary Examiner*—Jyoti Nagpaul
(74) *Attorney, Agent, or Firm*—Nixon Peabody LLP (57) ABSTRACT

An auto-calibration circuit or label (20) being adapted to be used with different first and second instruments. The first instrument being different from the second instrument. The auto-calibration label comprising first and second plurality of electrical connections. The first electrical connections conveys first instrument encoded-calibration information (82) corresponding to a sensor. The first instrument information is adapted to be utilized by the first instrument to auto-calibrate for the first sensor. The first plurality of electrical connections includes contact areas. The second electrical connections conveys second encoded-calibration information (84) corresponding to the first sensor. The second information is adapted to be utilized by the second instrument to auto-calibrate for the sensor. The second electrical connections includes a second plurality of contact areas, which are distinct from the first contact areas. The first electrical connections is adapted to be routed directly from each of the first contact areas to a first (52) or second common (54) connection. The second electrical connections is adapted to be routed directly from each of the second contact areas to the first or second common connection.

23 Claims, 6 Drawing Sheets

U.S. PATENT DOCUMENTS

| | | | |
|---|---|---|---|
| 5,575,403 A | 11/1996 | Charlton et al. | 221/31 |
| 5,597,532 A | 1/1997 | Connolly | 422/58 |
| 5,628,890 A | 5/1997 | Carter et al. | 204/403 |
| 5,630,986 A | 5/1997 | Charlton et al. | 422/64 |
| 5,700,695 A | 12/1997 | Yassinzadeh et al. | 436/180 |
| 5,856,195 A | 1/1999 | Charlton et al. | 436/50 |
| 6,102,872 A | 8/2000 | Doneen et al. | 600/582 |
| 6,531,040 B2 | 3/2003 | Musho et al. | 204/401 |

FOREIGN PATENT DOCUMENTS

| | | |
|---|---|---|
| EP | 1 174 716 A2 | 1/2002 |
| EP | 1 288 653 A1 | 3/2003 |
| EP | 1 398 631 A2 | 3/2004 |
| EP | 1 431 758 A1 | 6/2004 |
| WO | WO 2004/113911 A1 | 12/2004 |
| WO | WO 2004/113915 A1 | 12/2004 |

OTHER PUBLICATIONS

International Search Report corresponding to International Patent Application Serial No. PCT/US2006/014866, European Patent Office, dated Oct. 26, 2006, 4 pages.

AUTO-CALIBRATION LABEL AND METHOD OF FORMING THE SAME

CROSS-REFERENCE TO RELATED APPLICATIONS

This application claims priority to Application No. 60/672,764 filed on Apr. 19, 2005, which is incorporated by reference in its entirety.

FIELD OF THE INVENTION

The present invention generally relates to an auto-calibration circuit or label and methods of forming the same. The auto-calibration labels are used in automatically calibrating instruments or meters that determine the concentration of an analyte (e.g., glucose) in a fluid.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measures output.

Diagnostic systems, such as blood-glucose testing systems, typically calculate the actual glucose value based on a measured output and the known reactivity of the reagent-sensing element (test sensor) used to perform the test. The reactivity or lot-calibration information of the test sensor may be given to the user in several forms including a number or character that they enter into the instrument. One prior art method included using an element that is similar to a test sensor, but which was capable of being recognized as a calibration element by the instrument. The test element's information is read by the instrument or a memory element that is plugged into the instrument's microprocessor board for directly reading the test element.

These methods suffer from the disadvantage of relying on the user to enter the calibration information, which some users may not do. In this event, the test sensor may use the wrong calibration information and thus return an erroneous result. Improved systems use an auto-calibration label that is associated with the sensor package. The auto-calibration label is read automatically when the sensor package is placed in the meter and requires no user intervention.

The success of sensing instruments has lead to the development of improved sensing instruments and improved sensors. For example, existing sensing instruments analyze the sample for a predetermined length of time equal to approximately 30 seconds. New improved sensing instruments, however, are designed for much shorter analysis times (e.g., 5 seconds) and the calibration information for the test sensor measured at the 30 seconds analysis time is likely to be different from the calibration information relevant to shorter analysis time.

As new and improved instruments or meters are being developed and used by consumers, the older instruments or meters will still be used for an unknown period of time. If calibration codes adapted for characteristics of the new and improved instruments are used in older meters, test results may be inaccurate, which is undesirable. It would be desirable to provide a device and method that provides the lot calibration information of the test sensor to at least two instruments or meters in a reliable manner. It would also be desirable for this device to be as compact as possible as the label has to fit into the restricted space available on the sensor package.

SUMMARY OF THE INVENTION

According to one method, an auto-calibration circuit or label is formed and is adapted to be used with a first instrument and a second instrument. The first instrument is different from the second instrument and is adapted to determine an analyte concentration of a fluid sample. A first conductive ink pattern layer is supplied. A second conductive ink pattern layer is supplied and includes a first plurality of contact areas and a second plurality of contact areas. Insulating material is supplied and is located between the first and second conductive ink pattern layers. The first and second conductive ink pattern layers define first encoded-calibration information and second encoded-calibration information. The first and second encoded-calibration information is distinct. The first encoded-calibration information is adapted to be utilized by the first instrument to auto-calibrate. The second encoded-calibration information is adapted to be utilized by the second instrument to auto-calibrate.

According to one embodiment, an auto-calibration circuit or label is adapted to be used with a first instrument and a second instrument. The first instrument is different from the second instrument. The first and second instruments are adapted to determine an analyte concentration of a fluid sample. The auto-calibration label comprises a first plurality of electrical connections and a second plurality of electrical connections. The first plurality of electrical connections conveys first instrument encoded-calibration information corresponding to a first sensor. The first instrument encoded-calibration information is adapted to be utilized by the first instrument to auto-calibrate for the first sensor. The first plurality of electrical connections includes a first plurality of contact areas. The second plurality of electrical connections conveys second encoded-calibration information corresponding to the first sensor. The second encoded-calibration information is adapted to be utilized by the second instrument to auto-calibrate for the first sensor. The second plurality of electrical connections includes a second plurality of contact areas. The second plurality of contact areas is distinct from the first plurality of contact areas. The first plurality of electrical connections is adapted to be routed directly from each of the first plurality of contact areas to a respective first common connection or a second common connection. The second plurality of electrical connections is adapted to be routed directly from each of the second plurality of contact areas to the respective first common connection or the second common connection.

According to one embodiment, a sensor package is adapted to be used in a first instrument adapted to determine an analyte concentration in a fluid sample and in a second instrument adapted to determine the analyte concentration in the fluid sample. The first instrument is different from the second instrument. The sensor package comprises at least one sensor and an auto-calibration label. At least one sensor is adapted to receive the fluid sample and is operable with the first instrument and the second instrument.

The auto-calibration circuit or label is adapted to be used with the first instrument and the second instrument. The auto-calibration label includes a first plurality of electrical connections and a second plurality of electrical connections. The first plurality of electrical connections conveys first instrument encoded-calibration information corresponding to the at least one sensor. The first instrument encoded-calibration information is adapted to be utilized by the first instrument to auto-calibrate for the at least one sensor. The first plurality of electrical connections includes a first plurality of contact areas. The second plurality of electrical connections conveys second encoded-calibration information corresponding to the at least one sensor. The second encoded-calibration information is adapted to be utilized by a second instrument to auto-calibrate for the at least one sensor. The second plurality of electrical connections includes a second plurality of contact areas. The second plurality of contact areas is distinct from the first plurality of contact areas. The first plurality of electrical connections is adapted to be routed directly from each of the first plurality of contact areas to a respective first common connection or a second common connection. The second plurality of electrical connections is adapted to be routed directly from each of the second plurality of contact areas to the respective first common connection or the second common connection.

According to one embodiment, a system for determining an analyte concentration in a fluid sample comprises a test sensor, a processor, and an auto-calibration circuit or label. The test sensor is adapted to receive the fluid sample. The processor is responsive to the test sensor and is adapted to perform a predefined test sequence for measuring a predefined parameter value.

The auto-calibration circuit or label is coupled to the processor for providing first instrument encoded-calibration information and second instrument encoded-calibration information corresponding to the test sensor. The processor is adapted to read the first instrument encoded-calibration information and second instrument encoded-calibration information. The first and second information is utilized by the processor for each predefined test sequence. The first instrument-coded calibration information is defined by a first plurality of electrical connections. The first plurality of electrical connections includes a first plurality of contact areas. The second instrument-encoded calibration information is defined by a second plurality of electrical connections. The second plurality of contact areas is distinct from the first plurality of contact areas. The first plurality of electrical connections is adapted to be routed directly from each of the first plurality of contact areas to a respective first common connection or a second common connection. The second plurality of electrical connections is adapted to be routed directly from each of the second plurality of contact areas to the respective first common connection or the second common connection.

DETAILED DESCRIPTION OF ILLUSTRATED EMBODIMENTS

An instrument or meter in one embodiment uses a test sensor adapted to receive a fluid sample to be analyzed, and a processor adapted to perform a predefined test sequence for measuring a predefined parameter value. A memory is coupled to the processor for storing predefined parameter data values. Calibration information associated with the test sensor may be read by the processor before the fluid sample to be measured is received. Calibration information may be read by the processor after the fluid sample to be measured is received, but not after the concentration of the analyte has been determined. Calibration information is used in measuring the predefined parameter data value to compensate for different characteristics of test sensors, which will vary on a batch-to-batch basis. Variations of this process will be apparent to those of ordinary skill in the art from the teachings disclosed herein, including but not limited to, the drawings.

Figure 1:
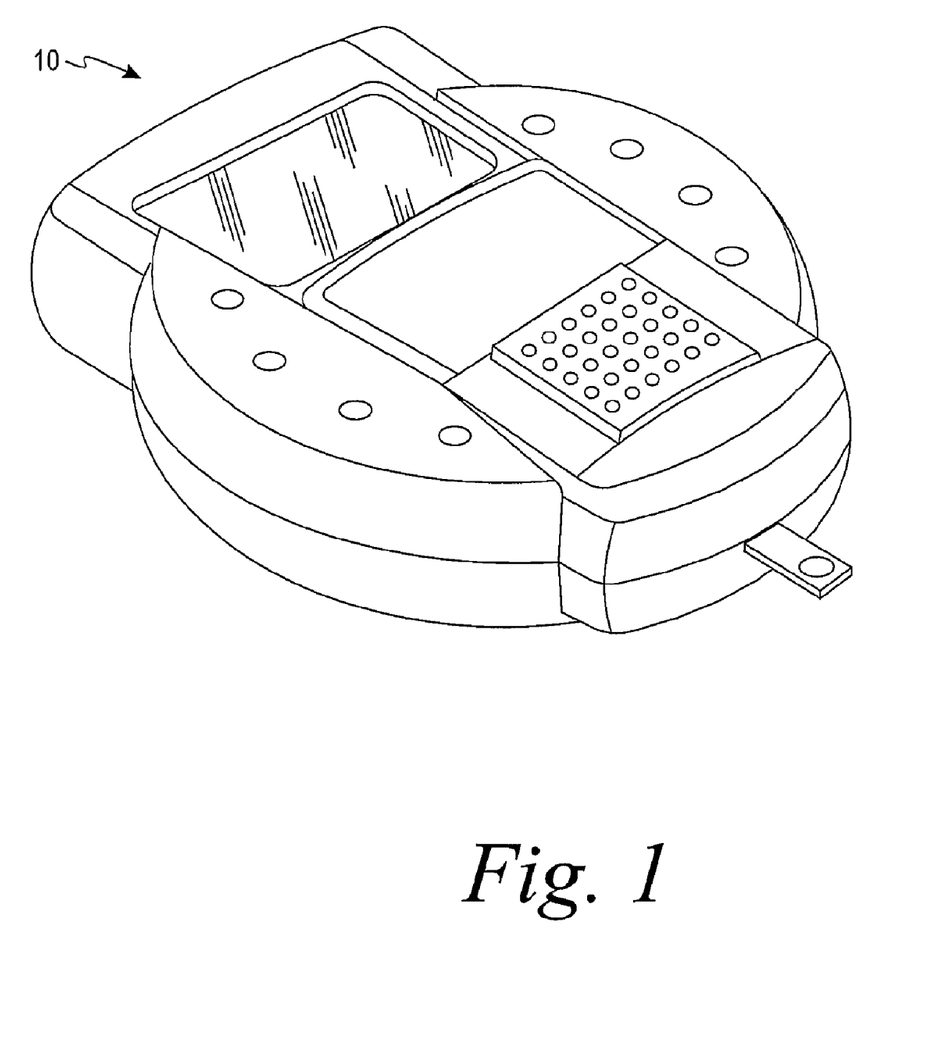
FIG. 1 shows a sensing instrument according to one embodiment.
Figure 2:
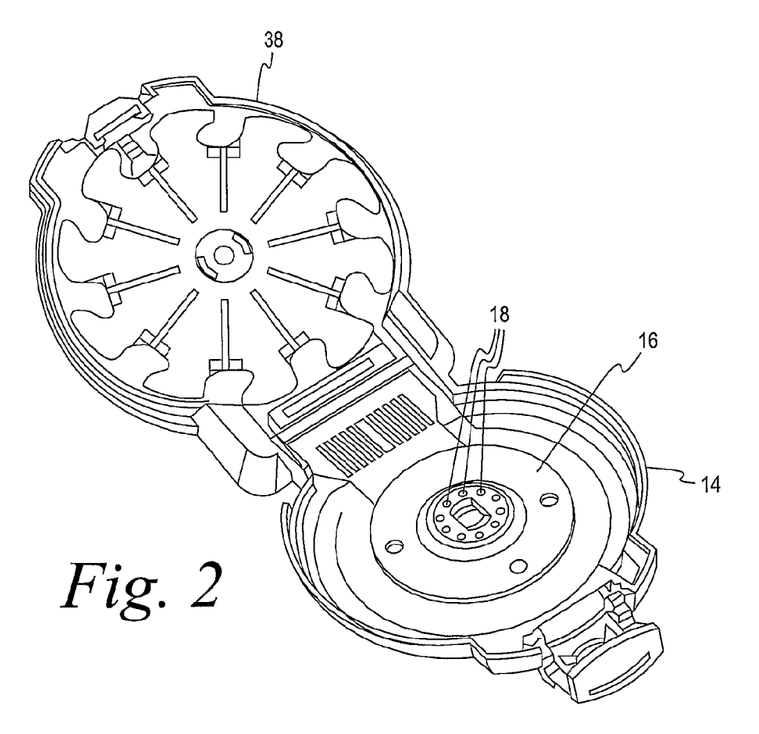
FIG. 2 shows the interior of the sensing instrument of FIG. 1.
Figure 3:
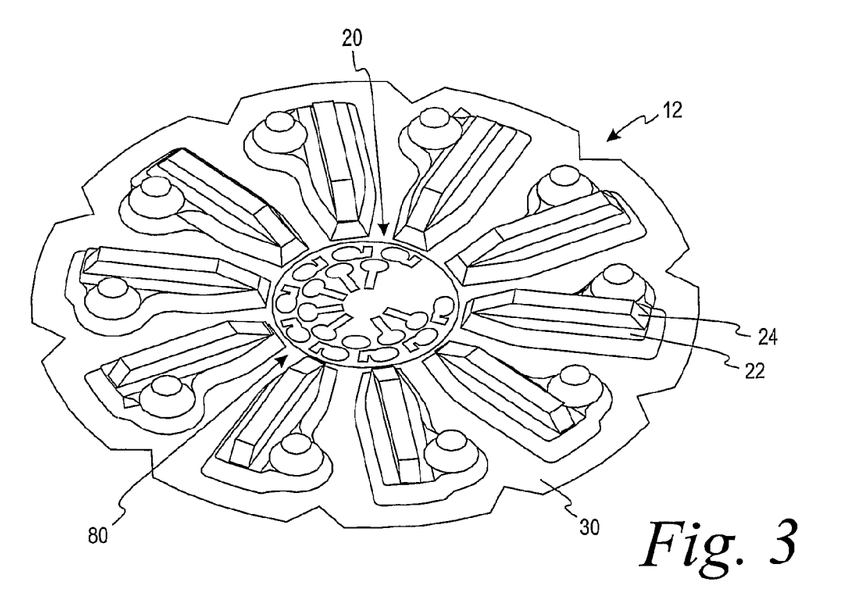
FIG. 3 shows a sensor package according to one embodiment for use with the sensing instrument of FIG. 2.

Referring now to FIGS. 1-3, an instrument or meter 10 is illustrated. In FIG. 2, the inside of the instrument 10 is shown in the absence of a sensor package. One example of a sensor package (sensor package 12) is separately illustrated in FIG. 3. Referring back to FIG. 2, a base member 14 of the instrument 10 supports an auto-calibration plate 16 and a predetermined number of auto-calibration pins 18. As shown in FIG. 2, for example, the instrument 10 includes ten auto-calibration pins 18. It is contemplated that the number of auto-calibration pins may vary in number and shape from that shown in FIG. 2. The auto-calibration pins 18 are connected for engagement with the sensor package 12.

The sensor package 12 of FIG. 3 includes an auto-calibration circuit or label 20 and a plurality of test sensors 22. The plurality of test sensors 22 is used to determine concentrations of analytes. Analytes that may be measured include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

In one embodiment, the plurality of test sensors 22 includes an appropriately selected enzyme to react with the desired analyte or analytes to be tested. An enzyme that may be used to react with glucose is glucose oxidase. It is contemplated that other enzymes may be used such as glucose dehydrogenase. An example of a test sensor is disclosed in U.S. Pat. No. 6,531,040 assigned to Bayer Corporation. It is contemplated that other test sensors may be used.

Calibration information or codes assigned for use in the clinical value computations to compensate for manufacturing variations between sensor lots are encoded on the auto-calibration circuit or label 20. The auto-calibration circuit or label 20 is used to automate the process of transferring calibration information (e.g., the lot specific reagent calibration information for the plurality of test sensors 22) such that the sensors 22 may be used with different instruments or meters. The auto-calibration pins 18 electrically couple with the auto-calibration circuit or label 20 when a cover 38 of the instrument 10 is closed and the circuit or label 20 is present. The auto-calibration circuit or label 20 will be discussed in detail in connection with FIGS. 4-7.

According to one method, an analyte concentration of a fluid sample is determined using electrical current readings and at least one equation. In this method, equation constants are identified using the calibration information or codes from the auto-calibration circuit or label 20. These constants may be identified by (a) using an algorithm to calculate the equation constants or (b) retrieving the equation constants from a lookup table for a particular predefined calibration code that is read from the auto-calibration circuit or label 20. The auto-calibration circuit or label 20 may be implemented by digital or analog techniques. In a digital implementation, the instrument assists in determining whether there is conductance along selected locations to determine the calibration information. In an analog implementation, the instrument assists in measuring the resistance along selected locations to determine the calibration information.

Referring back to FIG. 3, the plurality of test sensors 22 is arranged around the auto-calibration circuit or label 20 and extends radially from the area containing the circuit or label 20. The plurality of sensors 22 of FIG. 3 is stored in individual cavities or blisters 24 and read by associated sensor electronic circuitry before one of the plurality of test sensors 22 is used. The plurality of sensor cavities or blisters 24 extends toward a peripheral edge of the sensor package 12. In this embodiment, each sensor cavity 24 accommodates one of the plurality of test sensors 22.

The sensor package 12 of FIG. 3 is generally circular in shape with the sensor cavities 24 extending from near the outer peripheral edge toward and spaced apart from the center of the sensor package 12. It is contemplated, however, that the sensor package may be of different shapes then depicted in FIG. 3. For example, the sensor package may be a square, rectangle, other polygonal shapes, or non-polygonal shapes including oval.

With reference to FIGS. 4-7, the auto-calibration circuit or label 20 is adapted to be used with (a) the instrument or meter 10, (b) a second instrument or meter (not shown) being distinct or different from the instrument 10, and (c) the plurality of sensors 22 operable with both the instrument 10 and the second instrument. Thus, the auto-calibration circuit or label 20 may be considered as "backwards" compatible because it is adapted to be used with the second instrument (i.e., a new instrument) and the first instrument (i.e., an older instrument). The auto-calibration label may be used to work with two older instruments or two newer instruments. To reduce or avoid manufacturing modifications, it is desirable for a "backwards" compatible auto-calibration label not to increase the size of the label or decrease the size of the electrical contact areas.

The sensor package 12 contains a plurality of sensors 22 operable with the instrument 10 and the second instrument. Where the plurality of sensors 22 has essentially the same calibration characteristics, calibrating the instrument 10 for one of the sensors 22 is effective to calibrate the instrument 10 for each of the plurality of sensors 22 in that particular package 12.

Figure 5:
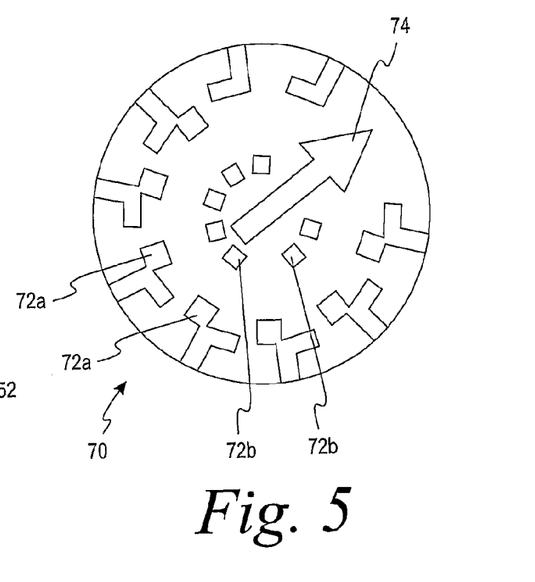
FIG. 5 shows an insulating layer according to one embodiment that will overlay the first pattern layer of FIG. 4.
Figures 6, 7:
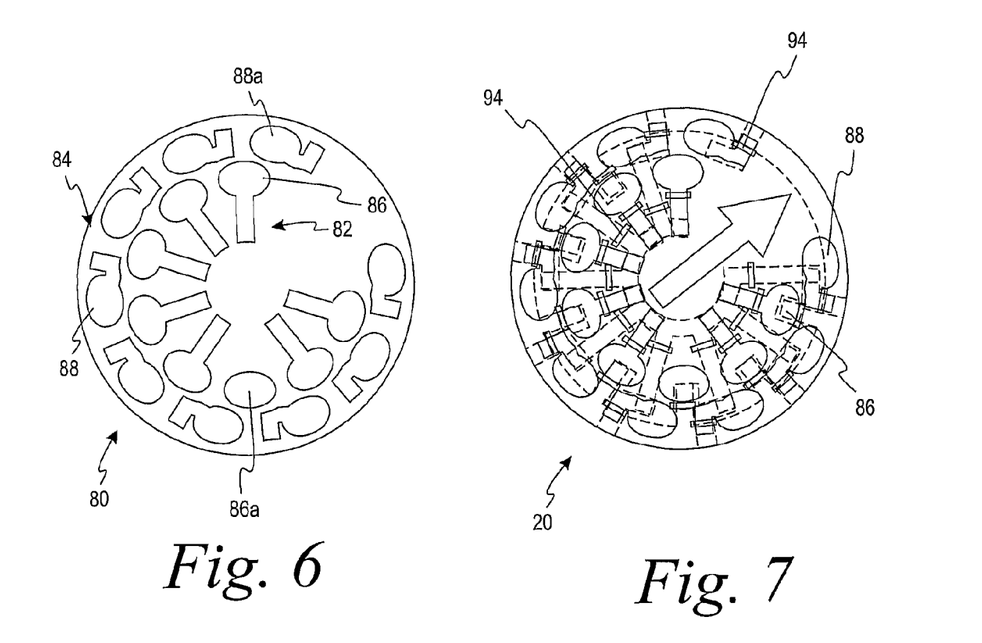
FIG. 6 shows a second pattern layer according to one embodiment that will overlay the insulating layer of FIG. 5.
FIG. 7 shows the layers illustrated in FIGS. 4-6 combined to form a final auto-calibrated label.
Figure 8:
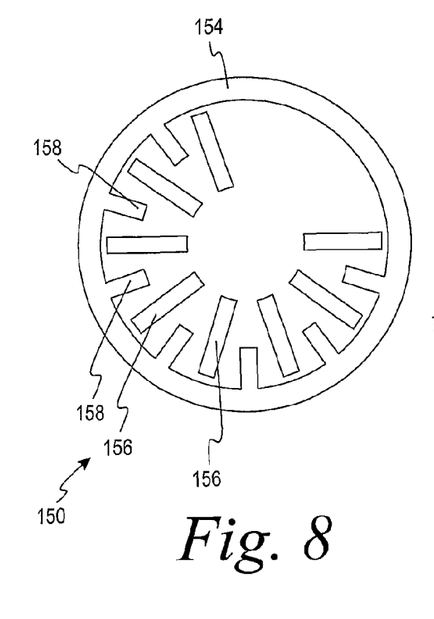
FIG. 8 shows a first pattern layer of an auto-calibration circuit or label according with another embodiment of the invention.
Figure 9:
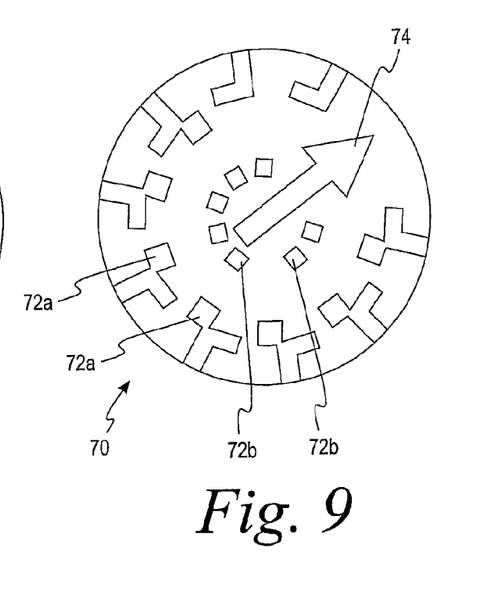
FIG. 9 shows an insulating layer in according to one embodiment that will overlay the first pattern layer of FIG. 8.
Figure 10:
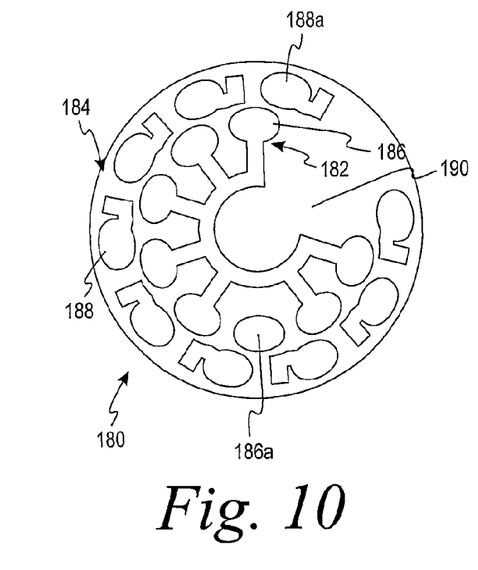
FIG. 10 shows a second pattern layer according to another embodiment that will overlay the insulating layer of FIG. 9.
Figure 11:
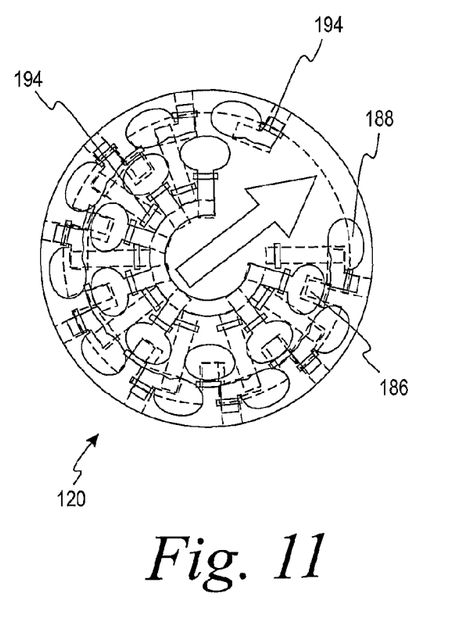
FIG. 11 shows the layers illustrated in FIGS. 8-10 combined to form a final auto-calibrated circuit or label.

In one embodiment, the auto-calibration circuit or label 20 (FIG. 7) comprises a first conductive ink pattern layer 50 (FIG. 4), an insulating layer 70 (FIG. 5), and a second conductive ink pattern layer 80 (FIG. 6). FIG. 7 illustrates the final auto-calibration circuit or label 20 after printing.

Figure 4:
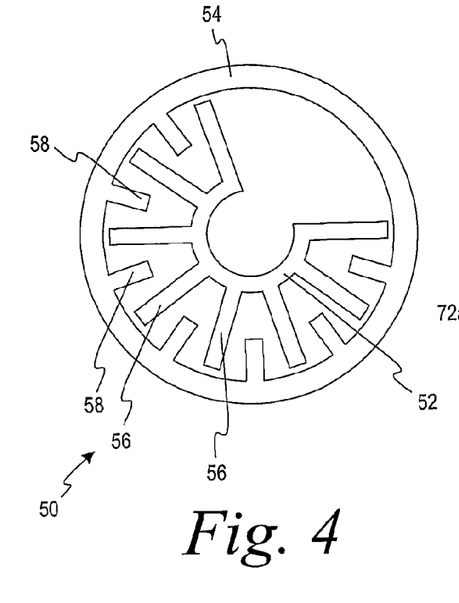
FIG. 4 shows a first pattern layer of an auto-calibration circuit or label according to one embodiment of the invention.

In this embodiment, the first conductive ink pattern layer includes a first common connection and a second connection. More specifically, the first conductive ink pattern layer 50 includes an inner ring 52 and an outer ring 54. For some applications, the inner ring 52 represents logical 0s and the outer ring 54 represents logical 1s. The inner ring 52 has a plurality of inner spokes 56 projecting radially outward therefrom. The outer ring 54 has a plurality of outer spokes 58 projecting radially inward therefrom. As will be discussed in more detail below, the plurality of inner spokes 56 assists in providing electrical paths to the inner ring 52, while the plurality of outer spokes 58 assists in providing electrical paths to the outer ring 54.

In this embodiment, conductive ink forms the inner ring 52, the outer ring 54, the plurality of inner spokes 56, and the plurality of outer spokes 58, while no ink is placed on spaces therebetween. In this embodiment, the first conductive ink pattern layer 50 is formed in the absence of contact areas (e.g., contact pads). It is contemplated that the inner ring or the outer ring may not be continuous. For example, the inner ring 52 is not continuous because it does not extend to form a complete circle. The outer ring 54, on the other hand, is continuous. It is contemplated that the inner ring and outer rings may be shapes other than circular. Thus, the term "ring" as used herein includes non-continuous structures and shapes other than circular.

The first conductive ink pattern 50 and second conductive ink pattern layer 80 include first instrument encoded-calibration information 82 and second instrument encoded-calibration information 84. The first instrument encoded-calibration information 82 corresponds to the plurality of test sensors 22. The first instrument encoded-calibration information 82 is adapted to be utilized by the instrument 10 to auto-calibrate. Thus, the instrument 10 is automatically calibrated to be used with the plurality of test sensors 22.

The second instrument encoded-calibration information 84 also corresponds to the plurality of sensors 22. The second instrument encoded-calibration information 84 is adapted to be utilized by the second instrument to auto-calibrate such that the second instrument is calibrated to be used with the plurality of test sensors 22. In this embodiment, the second instrument encoded-calibration information 84 is distinct (completely independent) from the first instrument encoded-calibration information 82 to account for different calibration characteristics between the first instrument 10 and the second instrument.

It will be understood, however, that use of the term "distinct" in this context may only mean that the encoded information is distinct, but the decoded information is essentially the same. For example, the instrument 10 may have essentially the same calibration characteristics, but the contacts (e.g., pins 18) to couple with the encoded information are located in different places for each instrument 10. Accordingly, the first and second instrument encoded-calibration information 82, 84 corresponding to each instrument 10 is distinct because the encoded information must be arranged to couple with the appropriate instrument.

According to one embodiment, the second conductive ink pattern layer 80 includes a plurality of inner contact areas 86 (e.g., contact pads) and a plurality of outer contact areas 88. In this embodiment, conductive ink forms the plurality of inner contact areas 86 and the plurality of outer contact areas 88 with no ink in the spaces therebetween. The second conductive ink pattern layer is in a generally radially-extending pattern. Specifically, the plurality of inner contact areas 86 and the plurality of outer contact areas 88 are in a generally radially-extending pattern. It is contemplated that other radially-extending patterns may be formed.

The second plurality of outer contact areas 88 is distinct from the first plurality of inner contact areas 86. The first plurality of electrical connections is adapted to be routed directly from each of the first plurality of inner contact areas 86 to a respective first common connection (e.g., inner ring 52) or a second common connection (e.g., outer ring 54). The second plurality of electrical connections is adapted to be routed directly from each of the second plurality of outer contact areas 88 to the respective first common connection (e.g., inner ring 52) or the second common connection (e.g., outer ring 54).

Thus, the electrical connections of the plurality of outer contact areas 88 are not routed through any of the plurality of inner contact areas 86. By having such an arrangement, additional independent encoded-calibration information may be obtained using the same total number of inner and outer contact areas 86, 88 without increasing the size of the auto-calibration label 20. Additionally, potential undesirable electrical connections may occur if the electrical connections of outer contact areas (e.g., outer pads) are routed through inner contact areas (e.g., inner pads).

Referring to FIG. 6, the second conductive ink pattern layer 80 is electrically coupled to the first instrument 10 via a plurality of inner contact areas 86 when the auto-calibration circuit or label 20 is positioned to be used by the first instrument 10. The second conductive ink pattern layer 80 is electrically coupled to the second instrument via a plurality of outer contact areas 88 when the auto-calibration circuit or label 20 is positioned to be used by the second instrument.

Referring also to FIG. 4, the plurality of inner spokes 56 assists in connecting the plurality of outer contact areas 88 to the inner ring 52. The plurality of outer spokes 58 assists in connecting the plurality of inner contact areas 86 to the outer ring 54.

According to one embodiment shown in FIGS. 4-7, substantially all of the plurality of outer contact areas 88 and the plurality of inner contact areas 86 are initially electrically connected to the inner ring 52 and the outer ring 54. To program the auto-calibration label, however, the conductive ink must be severed to break the electrical connection from the inner contact areas 86 to either the outer ring 54 or the inner ring 52 so that an individual inner contact area 86 is only connected to one of the inner or outer rings 52, 54. Similarly, to program the auto-calibration label, the conductive ink is typically severed to break the electrical connection from the outer contact area 88 to either the inner ring 52 or outer ring 54 so that an individual outer contact areas 88 is only connected to one of the inner or outer rings 52, 54. By having the inner or outer contact areas 86, 88 only connected to the inner or outer ring 52, 54 assists in maintaining a reliable instrument since any "no connect" may be sensed by the instrument software. Thus, a defective auto-calibration label or bad connection from the instrument may be automatically sensed by the instrument software.

The instrument may include several responses to reading the auto-calibration label. For example, responses may be include the following codes: (1) correct read, (2) misread, (3) non-read, defective code, (4) non-read, missing label, and (5) read code out-of-bounds. A correct read indicates that the instrument or meter correctly read the calibration information. A misread indicates that the instrument did not correctly read the calibration information encoded in the label. In a misread, the label passed the integrity checks. A non-read, defective code indicates that the instrument senses that a label is present (continuity between two or more auto-calibration pins), but the label code fails one or more encoding rules (label integrity checks). A non-read, missing label indicates that the instrument does not sense the presence of a label (no continuity between any of the auto-calibration pins). A read code out-of-bounds indicates that the instrument senses an auto-calibration code, but the calibration information is not valid for that instrument.

One method for severing the conductive ink is to break the electrical connection by using a laser cut. It is contemplated that other methods of breaking the electrical connection may be used such as punching holes through the label. As shown in FIG. 7, a number of potential cuts 94 are shown on the auto-calibration circuit or label 20 to form one particular pattern. The cuts 94 may be formed on the second conductive ink pattern layer 80 as shown in FIG. 7. Other patterns may be formed by performing different cuts than shown in FIG. 7.

It is also contemplated that the cuts may be formed on the first conductive ink pattern layer according to other methods. It is also contemplated that, conductive ink may be printed with the appropriate "gaps" such that breaking the electrical connection by, for example, laser cutting is unnecessary.

After selected ones of potential cuts 94 are formed, the plurality of outer contact areas 88 will be directly electrically connected to either the outer ring 54 or the inner ring 52. Similarly, after selected one of cuts 94 are formed, the plurality of inner contact areas 86 will be directly electrically connected to either the outer ring 54 or the inner ring 52. Typically, at least one of the outer contact areas 88 will always be directly electrically connected to the outer ring 54 or the inner ring 52 in the absence of cut 94. For example, outer contact area 88a is always directly electrically connected to the outer ring 54. Typically, at least one of the inner contact areas 86 will always be directly electrically connected to the outer ring 54 or the inner ring 52 in the absence of cut 94. For example, inner contact area 86a is always electrically connected to the outer ring 54.

In the auto-calibration circuit or label 20, the insulating layer 70 of FIG. 5 is used to isolate the first conductive ink pattern layer 50 and the second conductive ink pattern layer 80. The insulating layer 70 is formed from a dielectric layer that acts as an electrical insulator. The insulating layer 70 assists in electrically isolating the plurality of outer contact areas 88 from the outer ring 54. The insulating layer 70 also assists in electrically isolating the plurality of inner spokes 56 from the plurality of inner contact areas 86.

The insulating layer 70 forms first and second plurality of apertures 72a, 72b. The plurality of apertures 72a assists in directly electrically connecting the plurality of outer contact areas 88 with the outer ring 54. Similarly, the plurality of apertures 72a assists in directly electrically connecting the plurality of inner contact areas 86 with the outer ring 54. The plurality of apertures 72b assists in directly electrically connecting the plurality of inner contact areas 86 with the inner ring 52. Similarly, plurality of apertures 72b assists in directly electrically connecting the plurality of outer contact areas 88 with the inner ring 52. Electrical connections are made at locations where the conductive inks overlay the three layers 50, 70 and 80.

The insulating layer 70 also forms an aperture in the shape of an optional arrow 74. The function of the optional arrow 74 is to assist the consumer in aligning the auto-calibration circuit or label 20 when the sensor package 12 is placed in the instrument (e.g., instrument 10). It is contemplated that this function may be performed by shaped objects other than the optional arrow 74. Instead of being formed on the insulating layer 70, it is contemplated that the optional arrow 74 may be formed by, for example, a separate printed layer.

The auto-calibration circuit or label 20 of FIG. 7 is generally circular shaped. It is contemplated, however, that the auto-calibration circuit or label may be of different shapes than depicted in FIGS. 3-7. For example, the auto-calibration circuit or label may be a square, rectangle, other polygonal shapes, and non-polygonal shapes including oval.

Figure 12:
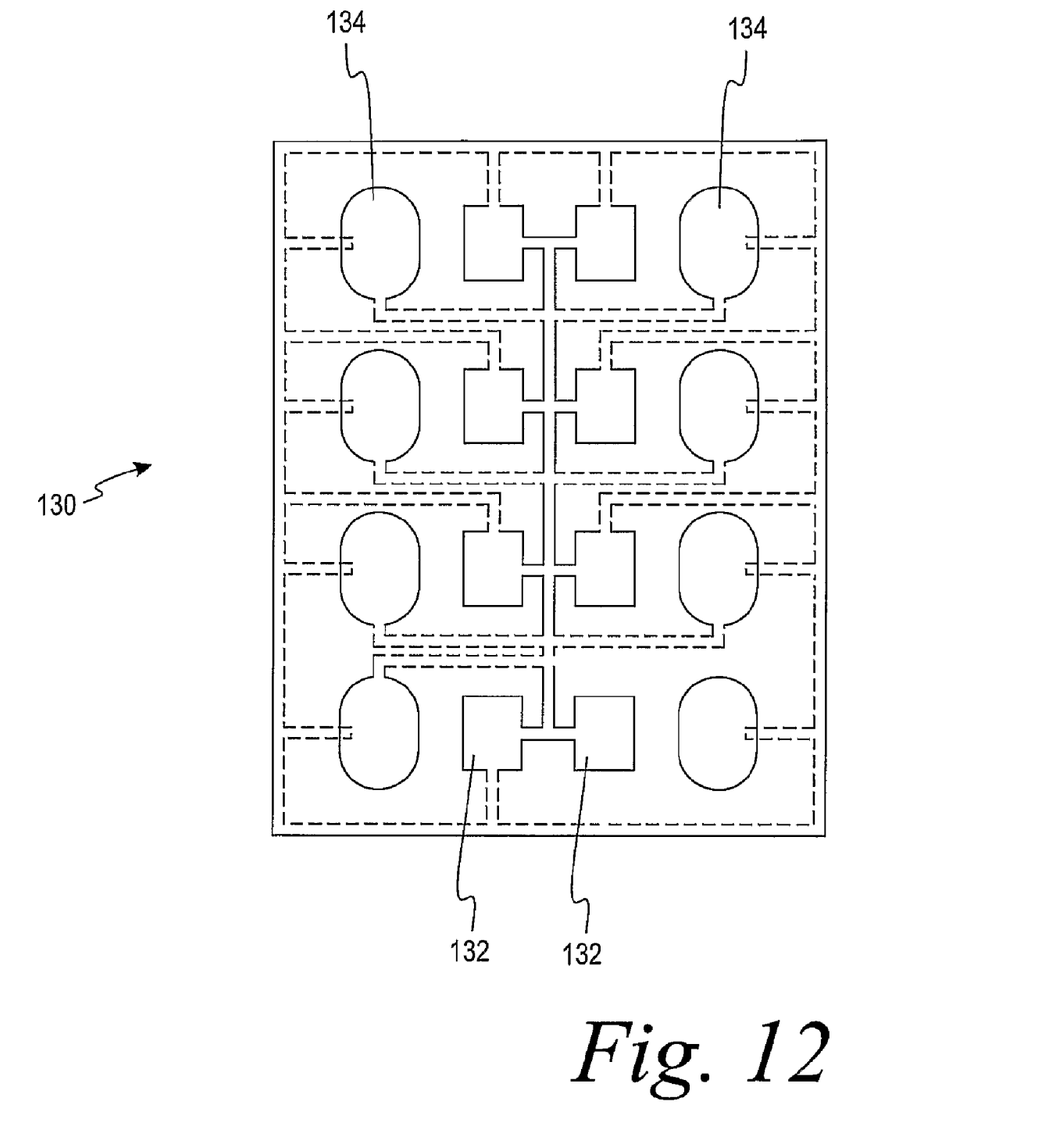
FIG. 12 shows a second pattern layer according to a further embodiment.

It is also contemplated that the contacts areas of the second conductive ink pattern layer may be in different locations than depicted in FIG. 6. For example, the second conductive ink pattern layer may be in a linear array. One example of such a second conductive ink pattern layer is shown in FIG. 12. FIG. 12 depicts a second conductive ink pattern layer 130 that includes a plurality of inner contact areas 132, a plurality of outer contact areas 134, a first common connection 136, and a second common connection 138. The second conductive ink pattern layer is shown as being generally rectangular in shape.

It is contemplated that the auto-calibration circuit or label 20 may be used with instruments other than instrument 10 depicted in FIGS. 1 and 2. The auto-calibration circuit or label 20 may also be used in other type of sensor packs than sensor package 12. For example, the auto-calibration circuit or label may be used in sensor packages such as a cartridge with a stacked plurality of test sensors or a drum-type sensor package.

According to another embodiment, the first common connection (e.g., inner ring) may be formed in the second conductive ink pattern layer instead of being formed in the first conductive ink pattern layer. Referring to FIGS. 8-11, an auto-calibration circuit or label 120 comprises a first conductive ink pattern layer 150, the insulating layer 70, and a second conductive ink pattern layer 180. The first conductive ink pattern layer 150 comprises an outer ring 154 with a plurality of outer spokes 158 and a plurality of inner spokes 156. The second conductive ink pattern layer 180 comprises an inner ring 190, a plurality of outer contact areas 188 and the plurality of inner contact areas 186. The auto-calibration circuit or label 120 with its first and second conductive ink pattern layers 150, 180 functions in a similar manner as described above in connection with the auto-calibration circuit or label 20.

Referring to FIGS. 13-16, an auto-calibration circuit or label 220 is shown according to a further embodiment. The auto-calibration circuit or label 220 is adapted to be used with (a) the instrument or meter 10, (b) a second instrument or meter (not shown) being distinct or different from the instrument 10, and (c) the plurality of sensors 22 operable with both the instrument 10 and the second instrument. Thus, the auto-calibration circuit or label 220 may be considered as "backwards" compatible because it is adapted to be used with the second instrument (i.e., a new instrument) and the first instrument (i.e., an older instrument). The auto-calibration label may be used to work with two older instruments or two newer instruments.

Figure 14:
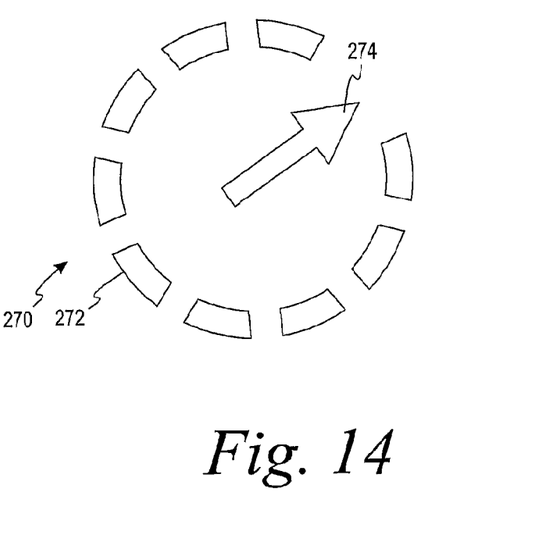
FIG. 14 shows insulating areas according to a further embodiment that will overlay the first pattern layer of FIG. 13.
Figure 15:
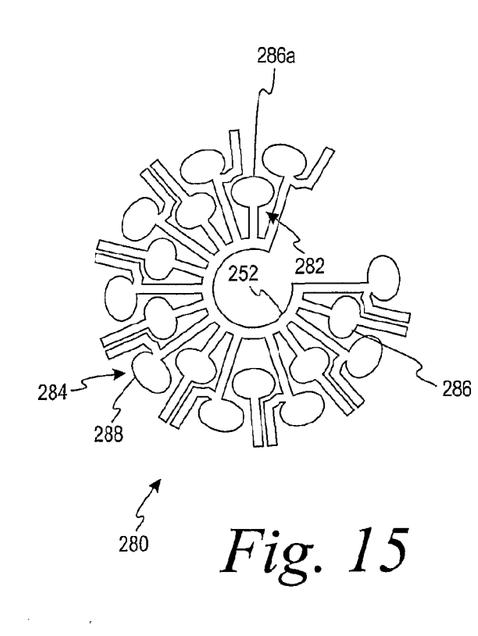
FIG. 15 shows a second pattern layer according to a further embodiment that will overlay the insulating areas of FIG. 14.
Figure 16:
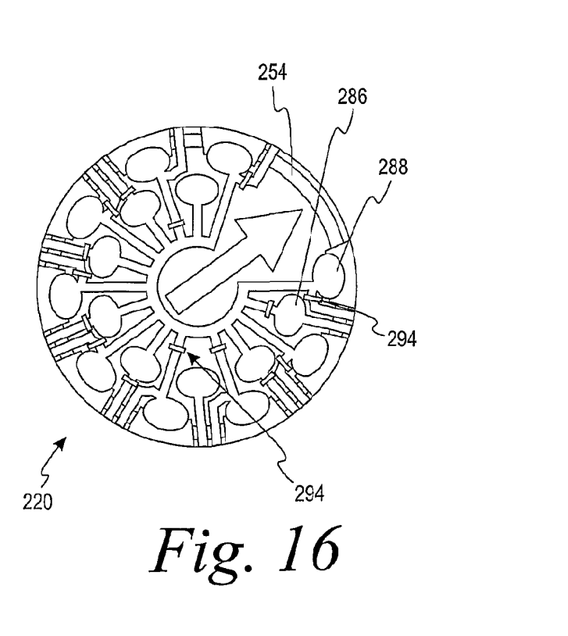
FIG. 16 shows the layers illustrated in FIGS. 13-15 combined to form a final auto-calibrated circuit or label.

In one embodiment, the auto-calibration circuit or label 220 (FIG. 16) comprises a first conductive ink pattern layer 250 (FIG. 13), insulating material 270 (FIG. 14), and a second conductive ink pattern layer 280 (FIG. 15). FIG. 16 illustrates the final auto-calibration circuit or label 220 after printing.

Figure 13:
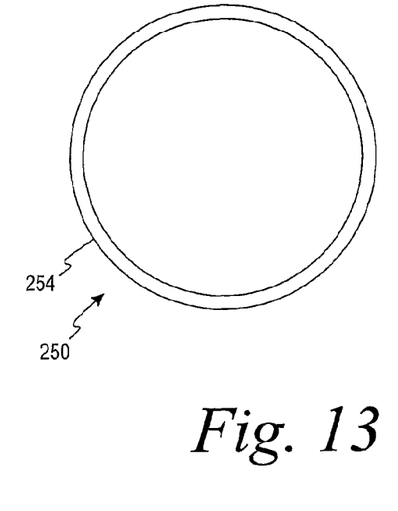
FIG. 13 shows a first pattern layer of an auto-calibration circuit or label according to a further embodiment of the invention.

In this embodiment, the first conductive ink pattern layer 250 includes a second common connection (e.g., outer ring 254). In this embodiment, conductive ink forms the outer ring 254 while no ink is placed on the remainder of the first conductive ink pattern layer. In this embodiment, the first conductive ink pattern layer 250 is formed in the absence of contact areas (e.g., contact pads). It is contemplated that the outer ring may not be continuous. It is contemplated that the outer ring may be shapes other than circular.

The first conductive ink pattern layer 250 and the second conductive ink pattern layer 280 include first instrument encoded-calibration information 282 and second instrument encoded-calibration information 284. The first instrument encoded-calibration information 282 corresponds to the plurality of test sensors 22. The first instrument encoded-calibration information 282 is adapted to be utilized by the instrument 10 to auto-calibrate. Thus, the instrument 10 is automatically calibrated to be used with the plurality of test sensors 22.

The second instrument encoded-calibration information 284 also corresponds to the plurality of sensors 22. The second instrument encoded-calibration information 284 is adapted to be utilized by the second instrument to auto-calibrate such that the second instrument is calibrated to be used with the plurality of test sensors 22. In this embodiment, the second instrument encoded-calibration information 284 is distinct (completely independent) from the first instrument encoded-calibration information 282 to account for different calibration characteristics between the first instrument 10 and the second instrument.

According to one embodiment, the second conductive ink pattern layer 280 includes a plurality of inner contact areas 286 (e.g., contact pads) and a plurality of outer contact areas 288. In this embodiment, conductive ink forms the plurality of inner contact areas 286 and the plurality of outer contact areas 288 with no ink in the spaces therebetween. The second conductive ink pattern layer is in a generally radially-extending pattern. Specifically, the plurality of inner contact areas 286 and the plurality of outer contact areas 288 are in a generally radially-extending pattern. It is contemplated that other radially-extending patterns may be formed.

The second plurality of outer contact areas 288 is distinct from the first plurality of inner contact areas 286. The first plurality of electrical connections is adapted to be routed directly from each of the first plurality of inner contact areas 286 to a respective first common connection (e.g., inner ring 252) or the second common connection (e.g., outer ring 254). The second plurality of electrical connections is adapted to be routed directly from each of the second plurality of outer contact areas 288 to the respective first common connection (e.g., inner ring 252) or the second common connection (e.g., outer ring 254).

Thus, the electrical connections of the plurality of outer contact areas 288 are not routed through any of the plurality of inner contact areas 286. By having such an arrangement, additional independent encoded-calibration information may be obtained using the same total number of inner and outer contact areas 286, 288 without increasing the size of the auto-calibration label 220. Additionally, potential undesirable electrical connections may occur if the electrical connections of outer contact areas (e.g., outer pads) are routed through inner contact areas (e.g., inner pads).

Referring to FIG. 15, the second conductive ink pattern layer 280 is electrically coupled to the first instrument 10 via a plurality of inner contact areas 286 when the auto-calibration circuit or label 220 is positioned to be used by the first instrument 10. The second conductive ink pattern layer 280 is electrically coupled to the second instrument via a plurality of outer contact areas 288 when the auto-calibration label 220 is positioned to be used by the second instrument.

According to the embodiment shown in FIGS. 13-16, substantially all of the plurality of outer contact areas 288 and the plurality of inner contact areas 286 are initially electrically connected to the inner ring 252 and the outer ring 254. To program the auto-calibration label, however, the conductive ink must be severed to break the electrical connection from the inner contact areas 286 to either the outer ring 254 or the inner ring 252 so that an individual inner contact area 286 is only connected to one of the inner or outer rings 252, 254. Similarly, to program the auto-calibration circuit or label, the conductive ink is typically severed to break the electrical connection from the outer contact areas 288 to either the inner ring 252 or outer ring 254 so that an individual outer contact area 288 is only connected to one of the inner or outer rings 252, 254. By having the inner or outer contact areas 286, 288 only connected to the inner or outer ring 252, 254 assists in maintaining a reliable instrument since any "no connect" may be sensed by the instrument software. Thus, a defective auto-calibration label or bad connection from the instrument may be automatically sensed by the instrument software.

One method for severing the conductive ink is to break the electrical connection by using a laser cut. It is contemplated that other methods of breaking the electrical connection may be used such as punching holes through the label. As shown in FIG. 16, a number of potential cuts 294 are shown on the auto-calibration circuit or label 220 to form one particular pattern. The cuts 294 may be formed on the second conductive ink pattern layer 280 as shown in FIG. 15. Other patterns may be formed by performing different cuts than shown in FIG. 16. It is also contemplated that the cuts may be formed on the first conductive ink pattern layer according to other methods. It is also contemplated that conductive ink may be printed with the appropriate "gaps" such that breaking the electrical connection by, for example, laser cutting is unnecessary.

After selected ones of potential cuts 294 are formed, the plurality of outer contact areas 288 will be directly electrically connected to either the outer ring 254 or the inner ring 252. Similarly, after selected one of cuts 294 are formed, the plurality of inner contact areas 286 will be directly electrically connected to either the outer ring 254 or the inner ring 252. Typically, at least one of the inner contact areas 286 and/or outer contact areas 288 will always be directly electrically connected to the outer ring 254 or the inner ring 252 in the absence of cut 294. For example, inner contact area 286a is always electrically connected to the inner ring 252.

In the auto-calibration circuit or label 220, the insulating material 270 of FIG. 14 is used to isolate the first conductive ink pattern layer 250 and the second conductive ink pattern layer 280. The insulating material 270 is formed from a dielectric layer that acts as an electrical insulator Specifically, the insulating material includes a plurality of insulating material areas 272. The insulating material 270 assists in electrically isolating the plurality of outer contact areas 288 from the outer ring 254. Electrical connections are made at locations where the conductive inks overlay the three layers 250, 270 and 280.

The insulating material 270 also forms an optional arrow 274. The function of the optional arrow 274 is to assist the consumer in aligning the auto-calibration circuit or label 220 when the sensor package 12 is placed in the instrument (e.g., instrument 10). It is contemplated that this function may be performed by shaped objects other than the optional arrow 274. Instead of being formed from the insulating material 270, it is contemplated that the optional arrow 274 may be formed by, for example, a separate printed layer.

The auto-calibration circuit or label 220 of FIG. 16 is generally circular shaped. It is contemplated, however, that the auto-calibration circuit or label may be of different shapes than depicted in FIGS. 13-16. For example, the auto-calibration circuit or label may be a square, rectangle, other polygonal shapes, and non-polygonal shapes including oval.

It is contemplated that the auto-calibration circuit or label 220 may be used with instruments other than instrument 10 depicted in FIGS. 1 and 2. The auto-calibration circuit or label 220 may also be used in other type of sensor packs than sensor package 12. For example, the auto-calibration circuit or label may be used in sensor packages such as a cartridge with a stacked plurality of test sensors or a drum-type sensor package.

According to one process, the auto-calibration circuit or labels 20, 120, 220 are formed by printing. In this method, the first conductive ink pattern layers, the insulating material, and the second conductive ink pattern layers are printed. The auto-calibration circuit or labels may be constructed by screenprinting conductive ink onto a base substrate, that may either be a separate substrate (not shown) or the sensor-package surface 30 of FIG. 3. A separate substrate may be attached to the sensor package 12 using, for example, an adhesive. Examples of adhesives include a hot melt, UV-cure or fast-curing adhesive. The auto-calibration circuit or labels 20, 120, 220 are desirably a carbon, silver or a carbon/silver blended ink. The sensor-package surface 30 may be any print-receptive surface including paper, polymer-filled paper or polymer substrate (e.g., a heat-stabilized polyethylene terephthalate (PET) or polycarbonate).

By printing, for example, the first and second encoded-calibration information 82, 84 of the second conductive ink pattern layer 80 in one pass, the manufacturing tolerances are improved. Specifically, since the plurality of inner contact areas 86 and the plurality of outer contact areas 88 are printed at the same time, they are in a fixed spatial relationship with each other.

It is contemplated that the auto-calibration circuit or labels 20, 120, 220 may be formed by other methods. For example, the auto-calibration circuit or label 20 may be formed by individually stamping the first conductive ink pattern layer, the insulating material, and the second conductive ink pattern layer and then connecting the layers together. In such a method, the layers may be connected together by, for example, an adhesive.

Alternative Process A

A method of forming an auto-calibration circuit or label adapted to be used with a first instrument and a second instrument, the first instrument being different from the second instrument and adapted to determine an analyte concentration of a fluid sample, the method comprising the acts of:
supplying a first conductive ink pattern layer;
supplying a second conductive ink pattern layer including a first plurality of contact areas and a second plurality of contact areas; and
supplying insulating material being located between the first and second conductive ink pattern layers,
wherein the first and second conductive ink pattern layers define first encoded-calibration information and second encoded-calibration information, the first and second encoded-calibration information being distinct, the first encoded-calibration information being adapted to be utilized by the first instrument to auto-calibrate, the second encoded-calibration information being adapted to be utilized by the second instrument to auto-calibrate.

Alternative Process B

The method of Alternative Process A wherein the first plurality of contact areas is distinct from the second plurality of contact areas.

Alternative Process C

The method of Alternative Process A wherein the auto-calibration circuit or label is generally circular shaped.

Alternative Process D

The method of Alternative Process A wherein the second conductive ink pattern layer is in a linear array.

Alternative Process E

The method of Alternative Process A wherein the second conductive ink pattern layer is in a generally radially-extending pattern.

Alternative Process F

The method of Alternative Process A wherein the first conductive ink pattern layer includes an inner ring and an outer ring.

Alternative Process G

The method of Alternative Process A wherein at least one of the inner ring and the outer ring is continuous.

Alternative Process H

The method of Alternative Process G wherein the outer ring is continuous.

Alternative Process I

The method of Alternative Process A wherein the first encoded-calibration information and the second encoded-calibration information are implemented by a digital technique to respective first and second instruments.

Alternative Process J

The method of Alternative Process A wherein the first encoded-calibration information and the second encoded-calibration information are implemented by a analog technique to respective first and second instruments.

Alternative Process K

The method of Alternative Process A wherein supplying the first conductive ink pattern layer includes printing the first conductive ink pattern layer, wherein supplying the second conductive ink pattern layer includes printing the second conductive ink pattern layer, wherein supplying the insulating material includes printing the insulating material.

Alternative Process L

The method of Alternative Process A wherein the insulating material is a plurality of insulating areas.

Alternative Process M

The method of Alternative Process A wherein the insulating material is an insulating layer that forms a plurality of apertures.

Alternative Embodiment N

An auto-calibration circuit or label being adapted to be used with a first instrument and a second instrument, the first instrument being different from the second instrument, the first and second instruments being adapted to determine an analyte concentration of a fluid sample, the auto-calibration label comprising:
a first plurality of electrical connections conveying first instrument encoded-calibration information corresponding to a first sensor, the first instrument encoded-calibration information being adapted to be utilized by the first instrument to auto-calibrate for the first sensor, the first plurality of electrical connections including a first plurality of contact areas; and
a second plurality of electrical connections conveying second encoded-calibration information corresponding to the first sensor, the second encoded-calibration information being adapted to be utilized by the second instrument to auto-calibrate for the first sensor, the second plurality of electrical connections including a second plurality of contact areas, the second plurality of contact areas being distinct from the first plurality of contact areas,
wherein the first plurality of electrical connections is adapted to be routed directly from each of the first plurality of contact areas to a respective first common connection or a second common connection,
wherein the second plurality of electrical connections is adapted to be routed directly from each of the second plurality of contact areas to the respective first common connection or the second common connection.

Alternative Embodiment O

The label of Alternative Embodiment N wherein the first plurality of electrical connections includes a plurality of outer contact areas and the second plurality of electrical connections includes a plurality of inner contact areas.

Alternative Embodiment P

The label of Alternative Embodiment N wherein the auto-calibration circuit or label is generally circular shaped.

Alternative Embodiment Q

The label of Alternative Embodiment N further including a first conductive ink pattern layer and a second conductive ink pattern layer that includes the first plurality and second plurality of electrical connections.

Alternative Embodiment R

The label of Alternative Embodiment Q wherein the first common connection is an inner ring and the second common connection is an outer ring.

Alternative Embodiment S

The label of Alternative Embodiment R wherein at least one of the inner ring and the outer ring is continuous.

Alternative Embodiment T

The label of Alternative Embodiment S wherein the outer ring is continuous.

Alternative Embodiment U

The label of Alternative Embodiment Q wherein the second conductive ink pattern layer is in linear array.

Alternative Embodiment V

The label of Alternative Embodiment Q wherein the second conductive ink pattern layer is in a generally radially-extending pattern.

Alternative Embodiment W

A sensor package adapted to be used in a first instrument adapted to determine an analyte concentration in a fluid sample and in a second instrument adapted to determine the analyte concentration in the fluid sample, the first instrument being different from the second instrument, the sensor package comprising:
at least one sensor being adapted to receive the fluid sample and being operable with the first instrument and the second instrument; and
an auto-calibration circuit or label being adapted to be used with the first instrument and the second instrument, the auto-calibration label including a first plurality of electrical connections and a second plurality of electrical connections, the first plurality of electrical connections conveying first instrument encoded-calibration information corresponding to the at least one sensor, the first instrument encoded-calibration information being adapted to be utilized by the first instrument to auto-calibrate for the at least one sensor, the first plurality of electrical connections including a first plurality of contact areas, the second plurality of electrical connections conveying second encoded-calibration information corresponding to the at least one sensor, the second encoded-calibration information being adapted to be utilized by a second instrument to auto-calibrate for the at least one sensor, the second plurality of electrical connections including a second plurality of contact areas, the second plurality of contact areas being distinct from the first plurality of contact areas,
wherein the first plurality of electrical connections is adapted to be routed directly from each of the first plurality of contact areas to a respective first common connection or a second common connection,
wherein the second plurality of electrical connections is adapted to be routed directly from each of the second plurality of contact areas to the respective first common connection or the second common connection.

Alternative Embodiment X

The sensor package of Alternative Embodiment W further including at least one cavity containing a respective one of the at least one sensor, the at least one cavity being arranged around the auto-calibration label.

Alternative Embodiment Y

The sensor package of Alternative Embodiment W wherein the at least one sensor is a plurality of test sensors and the at least one cavity is a plurality of cavities, each of the plurality of cavities containing a respective one of the plurality of sensors.

Alternative Embodiment Z

The sensor package of Alternative Embodiment W wherein the first plurality of electrical connections includes a plurality of outer contact areas and the second plurality of electrical connections includes a plurality of inner contact areas.

Alternative Embodiment AA

The sensor package of Alternative Embodiment W wherein the auto-calibration circuit or label is generally circular shaped.

Alternative Embodiment BB

The sensor package of Alternative Embodiment W further including a first conductive ink pattern layer and a second conductive ink pattern layer that includes the first plurality and second plurality of electrical connections.

Alternative Embodiment CC

The sensor package of Alternative Embodiment BB wherein the first common connection is an inner ring and the second common connection is an outer ring.

Alternative Embodiment DD

The sensor package of Alternative Embodiment CC wherein at least one of the inner ring and the outer ring is continuous.

Alternative Embodiment EE

The sensor package of Alternative Embodiment DD wherein the outer ring is continuous.

Alternative Embodiment FF

The sensor package of Alternative Embodiment W wherein the analyte is glucose.

Alternative Embodiment GG

A system for determining an analyte concentration in a fluid sample, the system comprising:
a test sensor adapted to receive the fluid sample;
a processor responsive to the test sensor and adapted to perform a predefined test sequence for measuring a predefined parameter value; and an auto-calibration circuit or label coupled to the processor for providing first instrument encoded-calibration information and second instrument encoded-calibration information corresponding to the test sensor, the processor being adapted to read the first instrument encoded-calibration information and second instrument encoded-calibration information, the first and second instrument-encoded calibration information being utilized by the processor for each predefined test sequence, the first instrument-encoded calibration information being defined by a first plurality of electrical connections, the first plurality of electrical connections including a first plurality of contact areas, the second instrument-encoded calibration information being defined by a second plurality of electrical connections, the second plurality of contact areas being distinct from the first plurality of contact areas, wherein the first plurality of electrical connections is adapted to be routed directly from each of the first plurality of contact areas to a respective first common connection or a second common connection, wherein the second plurality of electrical connections is adapted to be routed directly from each of the second plurality of contact areas to the respective first common connection or the second common connection.

Alternative Embodiment HH

The system of Alternative Embodiment GG wherein the analyte is glucose.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by the appended claims.

The invention claimed is:

1. A method of forming an auto-calibration circuit or label adapted to be used with a first instrument and a second instrument, the first instrument being different from the second instrument and adapted to determine an analyte concentration of a fluid sample, the method comprising the acts of:

supplying a first conductive ink pattern layer;

supplying a second conductive ink pattern layer including a first plurality of contact areas and a second plurality of contact areas; and supplying insulating material being located between the first and second conductive ink pattern layers, wherein the first conductive ink pattern layer and the first plurality of contact areas define first encoded-calibration information and the first conductive ink pattern layer and the second plurality of contact areas define second encoded-calibration information, the first encoded-calibration information being distinct from the second encoded-calibration information, the first encoded-calibration information is operable with the first instrument to auto-calibrate, the second encoded-calibration information is operable with the second instrument to auto-calibrate, wherein the first and second plurality of contact areas are located only on the second conductive ink pattern layer and the first conductive ink pattern layer is formed in the absence of contact areas.

2. The method of claim 1, wherein the first plurality of contact areas is distinct from the second plurality of contact areas.

3. The method of claim 1, wherein the second conductive ink pattern layer is in a linear array.

4. The method of claim 1, wherein the second conductive ink pattern layer is in a generally radially-extending pattern.

5. The method of claim 1, wherein the first conductive ink pattern layer includes an inner ring and an outer ring.

6. The method of claim 1, wherein at least one of the inner ring and the outer ring is continuous.

7. The method of claim 1, wherein the first encoded-calibration information and the second encoded-calibration information are implemented by a digital technique to respective first and second instruments.

8. The method of claim 1, wherein the first encoded-calibration information and the second encoded-calibration information are implemented by a analog technique to respective first and second instruments.

9. The method of claim 1, wherein supplying the first conductive ink pattern layer includes printing the first conductive ink pattern layer, wherein supplying the second conductive ink pattern layer includes printing the second conductive ink pattern layer, wherein supplying the insulating material includes printing the insulating material.

10. The method of claim 1, wherein the insulating material is a plurality of insulating areas.

11. An auto-calibration circuit or label being adapted to be used with a first instrument and a second instrument, the first instrument being different from the second instrument, the first and second instruments being adapted to determine an analyte concentration of a fluid sample, the auto-calibration label comprising:

a first plurality of electrical connections conveying first instrument encoded-calibration information corresponding to a first sensor, the first instrument encoded-calibration information is operable with the first instrument to auto-calibrate for the first sensor, the first plurality of electrical connections including a first plurality of contact areas; and a second plurality of electrical connections conveying second encoded-calibration information corresponding to the first sensor, the second encoded-calibration information is operable with the second instrument to auto-calibrate for the first sensor, the second plurality of electrical connections including a second plurality of contact areas, the second plurality of contact areas being distinct from the first plurality of contact areas, wherein the first plurality of electrical connections is routed directly from each of the first plurality of contact areas to a respective first common connection or a second common connection, wherein the second plurality of electrical connections is routed directly from each of the second plurality of contact areas to a respective one of the first common connection or the second common connection.

12. The label of claim 11, wherein the first plurality of electrical connections includes a plurality of outer contact areas and the second plurality of electrical connections includes a plurality of inner contact areas.

13. The label of claim 11, wherein the auto-calibration circuit or label is generally circular shaped.

14. The label of claim 11, further including a first conductive ink pattern layer and a second conductive ink pattern layer that includes the first plurality and second plurality of electrical connections.

15. The label of claim 14, wherein the first common connection is an inner ring and the second common connection is an outer ring.

16. The label of claim 15, wherein at least one of the inner ring and the outer ring is continuous.

17. A sensor package adapted to be used in a first instrument adapted to determine an analyte concentration in a fluid sample and in a second instrument adapted to determine the analyte concentration in the fluid sample, the first instrument being different from the second instrument, the sensor package comprising:
at least one sensor is operable to receive the fluid sample and operable with the first instrument and the second instrument; and
an auto-calibration circuit or label is operable with the first instrument and the second instrument, the auto-calibration label including a first plurality of electrical connections and a second plurality of electrical connections, the first plurality of electrical connections conveying first instrument encoded-calibration information corresponding to the at least one sensor, the first instrument encoded-calibration information is operable with the first instrument to auto-calibrate for the at least one sensor, the first plurality of electrical connections including a first plurality of contact areas, the second plurality of electrical connections conveying second encoded-calibration information corresponding to the at least one sensor, the second encoded-calibration information is operable with the second instrument to auto-calibrate for the at least one sensor, the second plurality of electrical connections including a second plurality of contact areas, the second plurality of contact areas being distinct from the first plurality of contact areas,
wherein the first plurality of electrical connections is routed directly from each of the first plurality of contact areas to a respective first common connection or a second common connection,
wherein the second plurality of electrical connections is routed directly from each of the second plurality of contact areas to a respective one of the first common connection or the second common connection.

18. The sensor package of claim 17, further including at least one cavity containing a respective one of the at least one sensor, the at least one cavity being arranged around the auto-calibration label.

19. The sensor package of claim 17, wherein the at least one sensor is a plurality of test sensors and the at least one cavity is a plurality of cavities, each of the plurality of cavities containing a respective one of the plurality of sensors.

20. The sensor package of claim 17, wherein the first plurality of electrical connections includes a plurality of outer contact areas and the second plurality of electrical connections includes a plurality of inner contact areas.

21. The sensor package of claim 17, further including a first conductive ink pattern layer and a second conductive ink pattern layer that includes the first plurality and second plurality of electrical connections.

22. The sensor package of claim 21, wherein the first common connection is an inner ring and the second common connection is an outer ring.

23. A system for determining an analyte concentration in a fluid sample, the system comprising:
a test sensor adapted to receive the fluid sample;
a processor responsive to the test sensor and adapted to perform a predefined test sequence for measuring a predefined parameter value; and
an auto-calibration circuit or label coupled to the processor for providing first instrument encoded-calibration information and second instrument encoded-calibration information corresponding to the test sensor, the processor operable to read the first instrument encoded-calibration information and second instrument encoded-calibration information, the first and second instrument-encoded calibration information operable with the processor for each predefined test sequence, the first instrument-encoded calibration information having a first plurality of electrical connections, the first plurality of electrical connections including a first plurality of contact areas, the second instrument-encoded calibration information having a second plurality of electrical connections, the second plurality of contact areas being distinct from the first plurality of contact areas,
wherein the first plurality of electrical connections is routed directly from each of the first plurality of contact areas to a respective first common connection or a second common connection,
wherein the second plurality of electrical connections is routed directly from each of the second plurality of contact areas to a respective one of the first common connection or the second common connection.

* * * * *